United States Patent [19]
Kyle

[11] Patent Number: 4,935,583
[45] Date of Patent: Jun. 19, 1990

[54] INSULATED CONDUCTOR WITH CERAMIC-CONNECTED ELEMENTS

[76] Inventor: James C. Kyle, 24372 Via San Clemente, Mission Viejo, Calif. 92692

[21] Appl. No.: 419,625

[22] Filed: Sep. 20, 1982

Related U.S. Application Data

[63] Continuation of Ser. No. 154,783, May 30, 1980, abandoned.

[51] Int. Cl.$^5$ .............................. H01B 17/26
[52] U.S. Cl. ............................... 174/152 GM
[58] Field of Search ............. 174/50.58, 50.61, 102 C, 174/105 R, 110 A, 113 C, 152 GM; 65/43, 49, 59.22, 59.34, 59.4; 428/385, 469

[56] References Cited

U.S. PATENT DOCUMENTS

| | | | |
|---|---|---|---|
| 2,197,511 | 4/1940 | Scharfnagel | 174/105 R |
| 2,577,576 | 12/1951 | Glickman et al. | 174/50.58 |
| 3,137,766 | 6/1964 | Teague | 174/110 A |
| 3,665,239 | 5/1972 | Morinaud | 174/50.61 |
| 3,854,827 | 12/1974 | Merz et al. | 174/152 GM |
| 3,977,857 | 8/1976 | Mattox | 174/152 GM |
| 4,220,814 | 9/1980 | Kyle et al. | 174/50.61 |
| 4,352,951 | 10/1982 | Kyle | 174/152 GM |

*Primary Examiner*—William E. Kamm
*Attorney, Agent, or Firm*—Ellsworth R. Roston; Charles H. Schwartz

[57] ABSTRACT

Electrical articles are provided in which an electrical conductor having a particular coefficient of thermal expansion is bonded to an electrical insulator having substantially the particular coefficient of thermal expansion. The bonding is provided by a ceramic material having substantially the particular coefficient of thermal expansion. By "substantially" is meant a close approximation to the particular coefficient of thermal expansion.

The electrical conductor may be made from platinum or titanium or a titanium alloy and the electrical insulator may be made from an alloy of magnesium oxide, silica and aluminum oxide designated as Fosterite. The ceramic material may be partially amorphous and partially crystalline.

The bonding may be accomplished by disposing the ceramic material between the electrical conductor and the electrical insulator and by subjecting the ceramic material to a controlled amount of heat. The heat may be applied by a laser beam for an instant such as a fraction of a second. The controlled application of heat causes the ceramic material to flow in the space between the electrical conductor and the electrical insulator and to bond the electrical conductor and the electrical insulator.

32 Claims, 4 Drawing Sheets

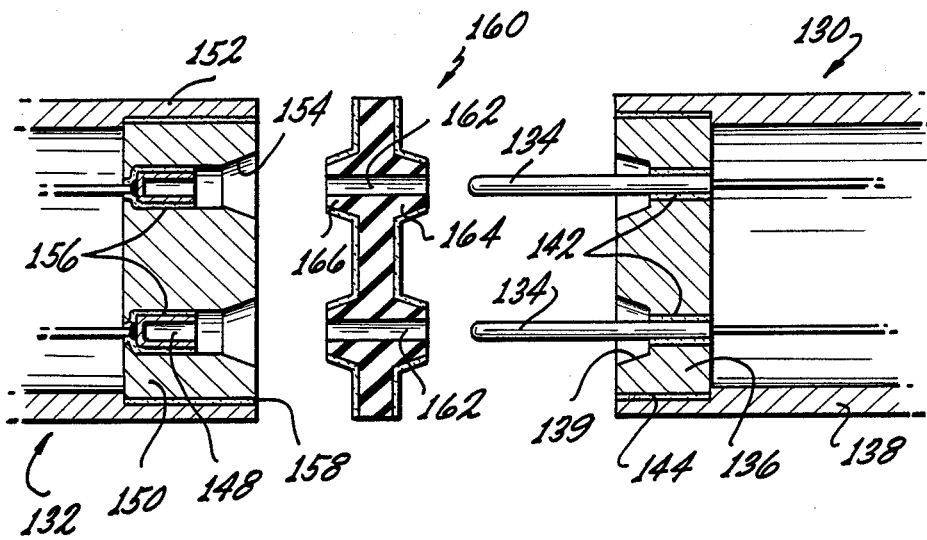
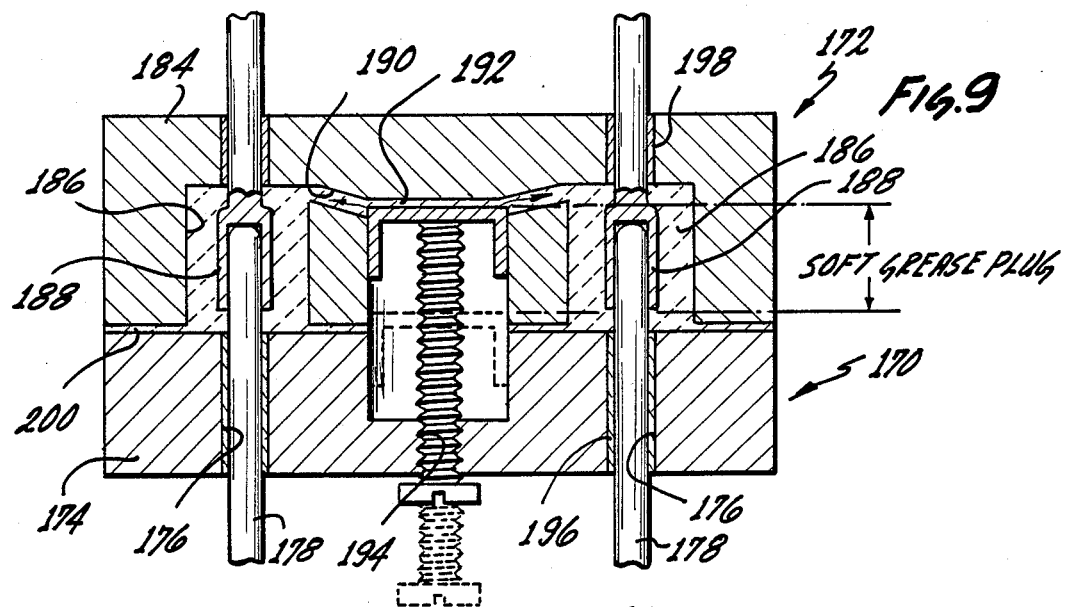
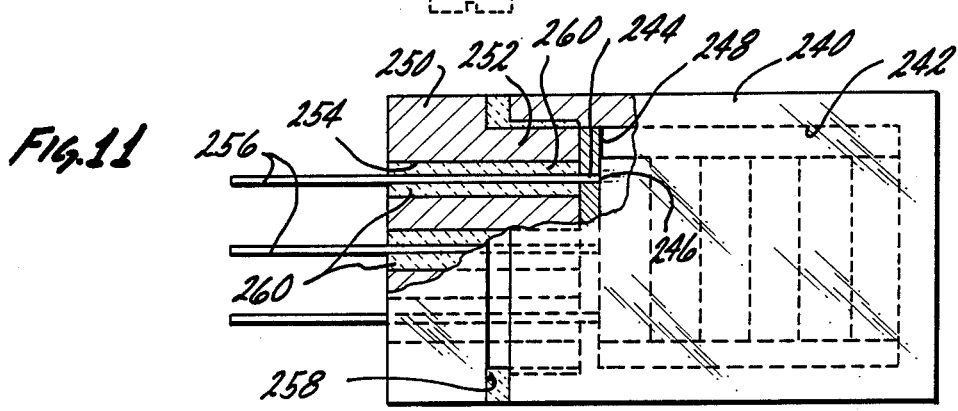

INSULATED CONDUCTOR WITH CERAMIC-CONNECTED ELEMENTS

This is a continuation of application Ser. No. 154,783 filed May 30, 1980, now abandoned.

This invention relates to an electrical terminal and more particularly to an electrical terminal in which an electrical conductor having a particular coefficient of thermal expansion is bonded to an electrical insulator having substantially the same coefficient of thermal expansion and the bonding is provided by a ceramic material having substantially the same coefficient of thermal expansion. The invention has wide applicability in a number of different fields. The invention also relates to a method of constructing such an electrical terminal.

Considerable work has been performed through the years to provide a satisfactory bond of an electrical conductor to an electrical insulator so that the bond will continue to exist under a wide range of different temperatures. The problem has arisen because the electrical conductor and the electrical insulator have had different coefficients of thermal expansion and because the bonding agent has had a coefficient of thermal expansion different from those of the conductor and the insulator. Because of this diversity in the coefficients of thermal expansion, one of the members in the resultant electrical terminal has been subjected to compressive forces to maintain the bond even with changes in temperatures. For example, when a ceramic material has been the bonding agent, the ceramic material has been subjected to compressive forces to maintain the bond even with the changes in temperature.

In spite of the considerable efforts which have been devoted through the years to provide a satisfactory bond between electrical conductors and electrical terminals through wide ranges of temperature, a satisfactory terminal has not yet been found. For example, the compressive forces imposed upon one or more of the members in the terminal have sometimes become excessive. This has caused that member or another member in the terminal to crack so that any seal between the members in the terminal has been destroyed. Sometimes, instead of cracking, one member in the terminal has tended to become separated from other members so as to destroy the electrical seal which is desired in the terminal.

This invention provides an electrical terminal which overcomes the problems described in the previous paragraphs. In the terminal of this invention, the seal produced in the terminal between the different members is maintained without any stress upon the members through a wide range of temperatures. For example, the terminal is able to maintain the seal without any undue forces on the terminal through a range of temperatures considerably below freezing to a range of temperatures considerably above the boiling point of water. The electrical terminal is maintained in a sealed relationship through this range of temperatures by providing an electrical conductor and an electrical insulator with substantially a particular coefficient of thermal expansion and by bonding to the conductor and the insulator a ceramic material with substantially the particular coefficient of thermal expansion. By "substantially" is meant a close approximation to the particular coefficient of thermal expansion. By way of illustration, the electrical conductor may be platinum, titanium or a titanium alloy and the electrical insulator may be a commonly known and used alloy of magnesium oxide, silica and alumina designated by the name "Fosterite".

The invention is also advantageous because the terminal of the invention can be formed simply and reliably. For example, the electrical conductor and the electrical terminal may be disposed in adjacent relationship and the ceramic material may be disposed in the space between the electrical conductor and the electrical insulator. A controlled amount of heat may then be applied to the ceramic material to melt the ceramic material and produce a flow of the ceramic material into the space between the electrical conductor and the electrical insulator. By way of illustration, the controlled amount of heat may be obtained by applying a laser beam to the ceramic material for an instant such as a fraction of a second. The ceramic material becomes bonded to the electrical insulator and the electrical conductor as a result of such application of heat.

In the drawings:

FIG. 8 is an exploded sectional view of still another embodiment of the invention;

FIG. 9 is a sectional view of a still further embodiment of the invention;

FIG. 11 is a schematic view of still another embodiment of the invention; and

Figure 1:
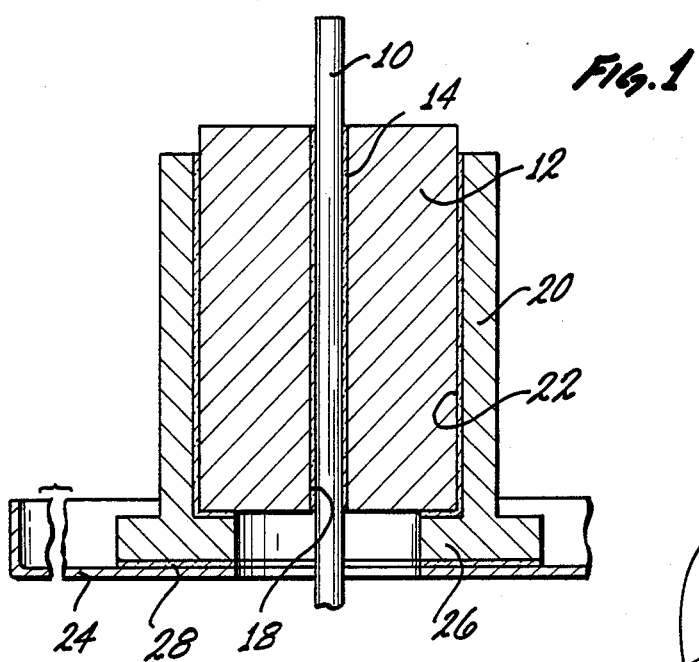
FIG. 1 is a sectional view of one embodiment of the invention.

In one embodiment of the invention, a conductor 10 made from a suitable material such as platinum is provided. An insulating material 12 may be provided with a bore 14 to receive the conductor 10. The insulating material 12 may be made from a suitable material constituting an alloy of magnesium oxide, silica and alumina. Such an alloy is commonly designated by the name "Fosterite". One common form of Fosterite may be obtained from Westman Ceramics and may be provided with the following composition:

| Material | Percentage by Weight |
|---|---|
| Calcine Montana Talc | 15 |
| Raw Montana Talc | 18 |
| Kaolin | 16 |
| Bentonite | 1 |
| Magnesite | 50 |

The insulating material 12 is advantageous because it has substantially the same coefficient of thermal expansion as platinum.

A ceramic material 18 may be disposed between the conductor 10 and the insulator 12 to bond the conductor and the insulator. The ceramic material 18 may have substantially the same coefficient of thermal expansion as the conductor 10 and the insulator 12. By way of illustration, the ceramic material may be provided with a composition such as disclosed in application Ser. No. 840,740 filed by me on Oct. 11, 1977 (now abandoned and replaced by continuation application Ser. No. 229,151), for a "Ceramic Material" and assigned of record to the assignee of record of this application. Such a ceramic material has certain important advantages. For example, it has a very high electrical resistivity and produces an excellent bond to the materials which it contacts, and it is also highly resistant to strong acids and bases.

This resistivity is as high as $10^{18}$ ohms.

As disclosed in application Ser. No. 840,740 (now abandoned and replaced by continuation application Ser. No. 229,151), the ceramic material is formed from first and second fluxes and a polycrystalline stuffing. The ceramic material may have the following composition:

| Material | Percentage |
| --- | --- |
| Flux A | |
| Lead oxide (PbO) | 68.5 |
| Boric oxide ($B_2O_2$) | 10.5 |
| Silicon dioxide ($SiO_2$) | 21.0 |
| Flux B | |
| Lead oxide (PbO) | 80 |
| Boric oxide ($B_2O_3$) | 20 |
| Stuffing Material | |
| Lead antimonate | 2 |
| Zinc zirconium silicate | 1 |
| Zirconium spinel | 1 |
| Zirconium silicate | 1 | and Flux A, Flux B and the stuffing material have the following percentages by weight in the mixture:

| Material | Percentage |
| --- | --- |
| Flux A | 15%–25% |
| Flux B | 40%–55% |
| Stuffing Material | 20%–45% |

Although the insulator 12 may constitute the external member in the terminal formed by the conductor 10 and the insulator 12, an electrical conductor 20 may be disposed externally of the insulator 12. The electrical conductor may be bonded to the insulator 12 by ceramic material 22 corresponding to the ceramic material 18. The conductor 20 may be made from a suitable material such as titanium or a titanium alloy. Titanium and alloys of titanium are advantageous because they have substantially the same coefficient of thermal expansion as platinum and the insulating material designated as "Fosterite". The conductor 20 may also be coated with platinum or an alloy of platinum and bismuth. A lid 24 may be disposed on a flange 26 provided on the conductor 20. The lid 24 may be sealed to the flange 26 by ceramic material 28 corresponding to the ceramic material 18 and 22.

The terminal described above may be formed by assembling the members and disposing ceramic material between the conductor 10 and the insulator 12 and between the insulator 12 and the conductor 20. A controlled amount of heat may then be applied to the ceramic material 18 and the ceramic material 22 to melt the ceramic material and produce a flow of the ceramic material into the space between the conductor 10 and the insulator 12 and between the insulator 12 and the conductor 20. For example, the controlled amount of heat may be sufficient to produce a temperature of approximately 1500° F. to 1750° F. in the ceramic material. When the ceramic material flows between the conductor 10 and the insulator 12 and between the insulator 12 and the conductor 20, it becomes bonded to the conductor 10 and the insulator 12 and to the insulator 12 and the conductor 20. By way of illustration, the controlled amount of heat may be obtained by directing a laser beam to the ceramic material 18 and the ceramic material 22 for an instant such as a fraction of a second. Under such controlled conditions of heat, the ceramic material may have properties of providing a hermetic seal even when subjected to temperatures such as approximately 1200° F. for an extended period such as approximately one hundred (100) hours.

The terminal described above has certain advantages, particularly when formed by the method described above. For example, the conductor 10, the insulator 12 and the conductor 20 have substantially the same coefficient of thermal expansion. Because of this, the ceramic material 18 can be bonded to the conductor 10 and the insulator 12, and the ceramic material 22 can be bonded to the insulator 12 and the conductor 20, without subjecting the ceramic material or any other of the components in the terminal to compression. Since all of the different elements in the terminal have substantially the same coefficient of expansion, they can react in substantially the same manner to considerable changes in temperature without subjecting any of the elements to excessive forces which will tend to crack such elements or separate such elements from other elements in the terminal.

The terminal described above has particular utility in a heart pacemaker. The terminal can be disposed on a heart pacemaker to seal the heart pacemaker and to provide for an insertion of the heart pacemaker into the body of a patient without any negative response of the body to any of the materials in the terminal. In other words, materials such as platinum, titanium, titanium alloy, "Fosterite" and the ceramic material used in the embodiment shown in FIG. 1 and described above do not produce any adverse reaction of the human body. When the terminal is used in a heart pacemaker, the platinum conductor 10 is connected to a terminal which is introduced to the heart and the titanium conductor 20 is effective as a ground terminal.

It will be appreciated that a terminal formed by the insulator 12 and the conductor 20 is within the scope of this invention even when the conductor 10 is not included. In other words, the insulator 12 may be disposed within a conductor which may be made from a suitable material such as platinum, titanium or a titanium alloy. Specifically, the terminal is within the scope of the invention whether the conductor is within the insulator or external to the insulator.

The embodiment shown in FIG. 1 includes a single conductor 10. Terminals may also be provided within the scope of the invention wherein a plurality of conductors may be included. For example, in the embodiment shown in FIG. 2, holes 30 are provided in an electrical insulator 32 made from a suitable material such as the alloy of magnesium oxide and alumina. An electrical conductor 34 may be extended through each of the holes. The electrical conductors 34 may be made from platinum or titanium or a titanium alloy. Each of the conductors 34 is sealed to the insulator 30 by a ceramic material 36 such as described above. In this way, a terminal with a multiple number of feed-through wires may be hermetically sealed to the insulating cap 30 without any requirement that the conductors 34 be precisely positioned within the holes 32. As a result, any requirement for the use of fixtures to properly position the conductors 34 within the holes 32 is eliminated. Although the cap 30 has been described as being made from insulating material, it may also be made from a suitable metal such as titanium or a titanium alloy without departing from the scope of the invention.

It will be appreciated that a considerable number of conductors 34 may be disposed within the insulating cap 30. For example, when the embodiment shown in FIG. 2 and described above is to be used for brain implants, approximately 16 to 64 conductors may be provided to serve as different leads. These leads are connected to different portions of the brain to create a package for stimulating auditory nerves in the brain. The stimulation of the auditory nerves in the brain provides for the operation of the brain in indicating to a deaf patient the characteristics of spoken words without the patient actually having heard the words.

Figure 2:
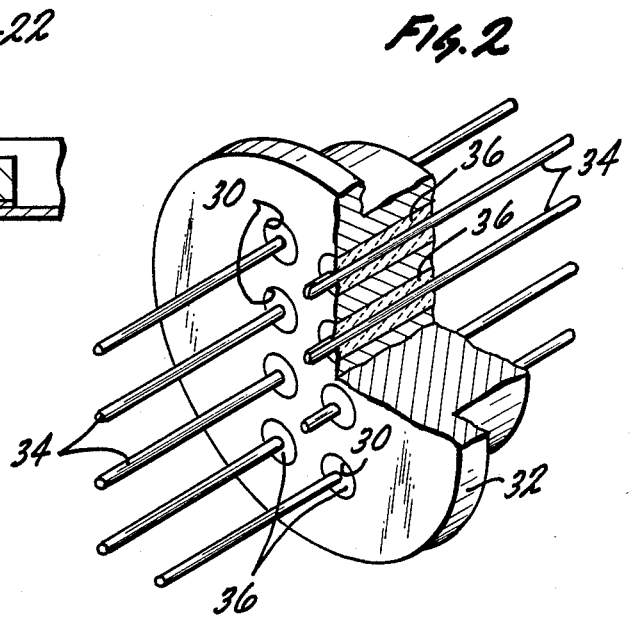
FIG. 2 is a perspective view, partially broken away, of a second embodiment of the invention.

The embodiment shown in FIG. 2 has certain important advantages. It provides apparatus which can be disposed near the brain without creating disturbances in the body or the brain because of the disposition of foreign matter in the body. The ability of the apparatus to be disposed in the body results from the fact that all of the materials in the apparatus are compatible with the body. The embodiment is further advantageous because it provides an electrical insulator which is predictable in shrinkage dimensions to a very small value such as ±0.001 inch. This results in part because the insulating material made from the alloy of magnesium oxide, silica and alumina has been fired at a relatively high temperature such as approximately 2000° F.

Figure 3:
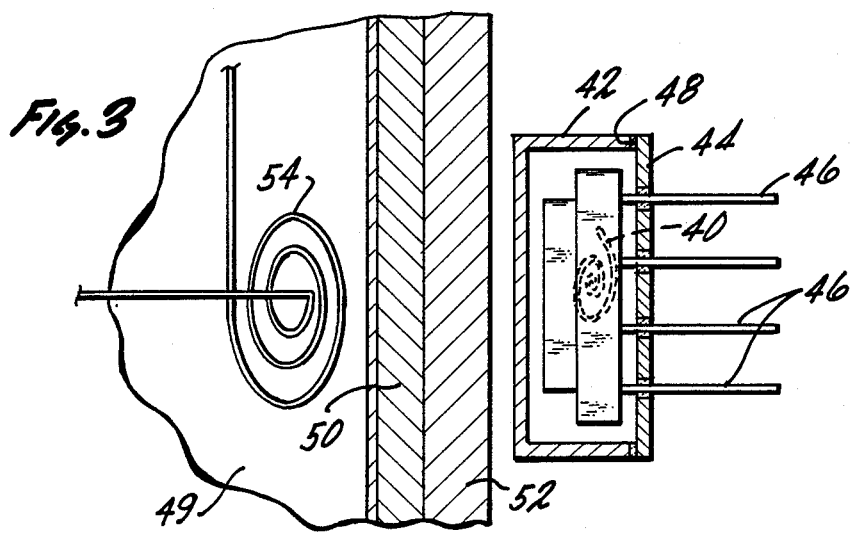
FIG. 3 is a sectional view of a third embodiment of the invention.

The embodiment shown in FIG. 3 may also be used in brain implants. This embodiment includes a coil 40 disposed in a receptacle which is formed by a casing 42 and a cover 44. The casing 42 and the cover 44 may be made from g titanium or an alloy of titanium. Leads 46 made from a suitable electrical conductor such as platinum or titanium or a titanium alloy extend from the coil 40 to different auditory nerves in the brain. The casing 42 and the cover 44 are sealed to each other by ceramic material 48 made from a suitable material such as described above. Ceramic material is also disposed between each of the leads 46 and the cover 44 to seal the leads to the cover.

The unit described in the previous paragraph is made from different materials, all of which are compatible with the tissue in the body. As a result, the unit does not produce any adverse effects in the body when the unit is inserted into the body. For example, the unit may be inserted into the head at a position interior to skin 49, tissue 50 and bone structure 52 in the head of the patient. In this way, the coil 40 can respond magnetically to signals introduced to a coil 54 which is disposed exterior to the body of the patient. The signals introduced to the coil 54 represent different sounds which are intended to stimulate the auditory nerves of the patient and produce a response of the patient as if the patient were directly listening to sounds.

Figure 4:
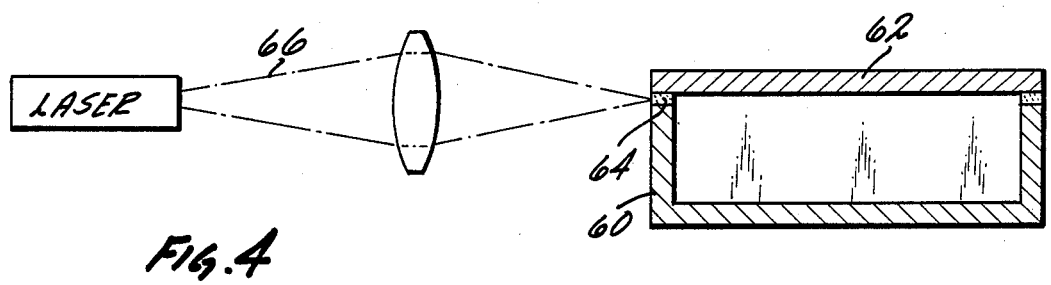
FIG. 4 is a schematic view of apparatus for producing a seal in the different embodiments of the invention.

FIG. 4 illustrates a method of welding a casing 60 to a cover 62 by focusing heat on ceramic material 64 disposed between the casing and the cover. For example, a laser beam 66 may be directed to the ceramic material to produce a flow of the ceramic material in the space between the casing 60 and the cover 62. It will be appreciated that any other source of focused heat such as infrared energy obtained from a quartz source may be used. It will also be appreciated that any other pair of members within the scope of the invention may be bonded by similar techniques.

Figure 5:
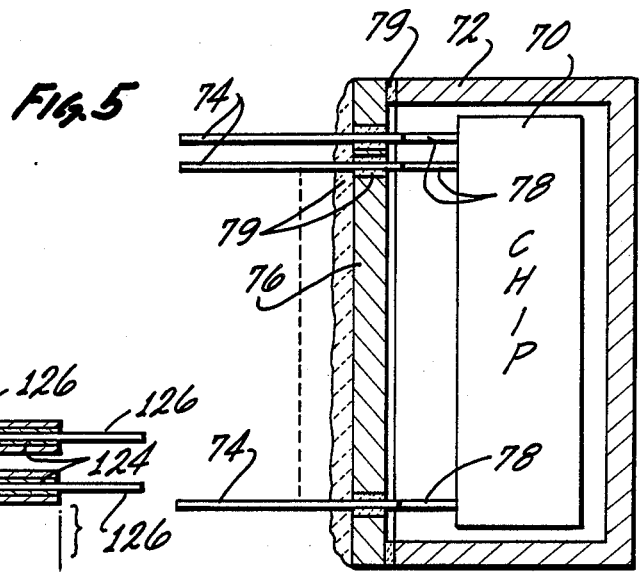
FIG. 5 is a sectional view of a further embodiment of the invention.

FIG. 5 illustrates an arrangement somewhat similar to that shown in FIG. 3. In the embodiment of FIG. 5, a semiconductor chip or semiconductor chips 70 are disposed in a casing 72 made from a suitable material such as the alloy of magnesium oxide and alumina. A plurality of leads 74 made from a suitable material such as gold extend from the chip 70 to a cover 76 preferably made from the same material as the casing 72. The leads 74 are bonded as by ultrasonic energy to leads 78 which may be made from a suitable material such as platinum. The leads 78 may be provided with an insulating coating made from a suitable material such as a polyamide or petrofluoroethylene (such as designated by the trademark "Teflon") or a silicone. The cover 76 may be sealed to the casing 72 by ceramic material 79 and the leads 74 and the leads 78 may be sealed to the cover 76 by ceramic material corresponding to the ceramic material 79.

Figure 6:
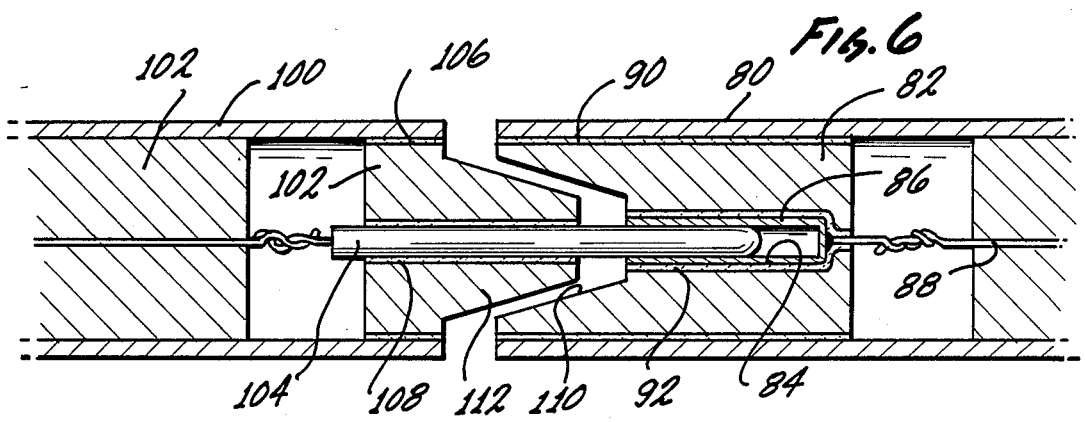
FIG. 6 is a partially exploded sectional view of an additional embodiment of the invention.

FIG. 6 illustrates an embodiment which constitutes a coaxial cable. The cable includes a metallic sheath 80 made from a suitable material such as titanium or a titanium alloy. An electrical insulator 82 made from a suitable material such as the alloy of magnesium oxide, silica and alumina is disposed in the sheet 80. The insulator 82 is provided with a bore 84 which receives a female conductor 86 and a terminal 88 extending from the female conductor 86. The sheath 80 and the insulator 82 are sealed by a ceramic material 90 and the female terminal 86 and the terminal 88 are sealed to the insulator 82 by ceramic material 92.

A sheath 100, an insulator 102 and a male conductor 104 are formed in a manner similar to that described in the previous paragraph. For example, ceramic material 106 bonds the insulator 102 to the sheath 100 and ceramic material 108 bonds the male conductor 104 to the insulator 102. The male conductor 104 extends beyond the insulator 102 so that it can be extended into the female conductor 86 to provide electrical connection with the female conductor. The electrical coupling between the male conductor 108 and the female conductor 86 is facilitated by providing a socket 110 at one end of the insulator 82 and by providing a corresponding projection 112 at the corresponding end of the insulator 102.

Figure 7:
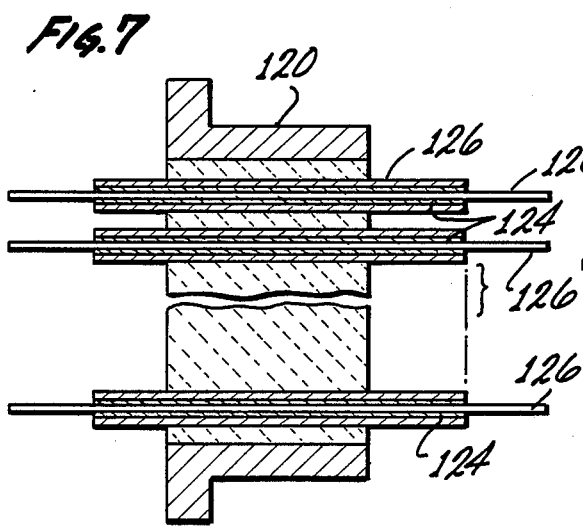
FIG. 7 is a sectional view of a further embodiment of the invention.

FIG. 7 shows an arrangement by which a plurality of cables can be disposed in fixed relationship to one another within a sleeve 120. The sleeve 120 may be made from a suitable material such as titanium or a titanium alloy and may be provided with a relatively large diameter to receive a plurality of cables. Each of the cables may be provided with a central conductor 122, an electrical insulator 124 enveloping the conductor 122 and a sheath 126 enveloping the insulator 124. The conductor 122 may be made from a suitable material such as platinum and the sheath 126 may be made from a suitable material such as titanium or a titanium alloy. The conductor 122 is sealed to the insulator 124 by ceramic material and the insulator 124 is sealed to the sheet 126 by ceramic material. Ceramic material may also be disposed within the sleeve 120 as a filler between the different sheaths 126 and may be sealed to the members which it contacts.

As will be seen, the embodiment shown in FIG. 7 offers certain advantages. It provides for the formation of a plurality of cables by relatively simple methods and further provides for the disposition and sealing of the sheaths within the sleeve 120 by relatively simple methods. Furthermore, if any of the individual cables is not properly sealed, sealing can be provided by subjecting the ceramic material within the cable to additional heat. Additional heat can also be applied to the ceramic material within the sleeve 120 to effectuate a seal of the different cables within the sleeve if such a seal has not been previously provided.

FIG. 8 shows an arrangement for producing an electrical connector which can be disposed within water, even at deep levels, to provide a water resistant underwater system. The connector includes a male member generally indicated at 130 and a female member generally indicated at 132. The male member 130 includes electrically conductive pins 134, an electrical insulator 136 and an electrically conductive sheath 138. The insulator 136 is preferably provided with sockets 139 at one end of the insulator at positions around each of the terminals 134. The terminals 134 are sealed to the insulator 136 by ceramic material 142 and the sheath 138 is sealed to the insulator 136 by ceramic material 144.

The female member 132 is provided with female terminals 148 constructed to receive the pins 134 in press-fit relationship. The female member 132 is also provided with an insulator 150 and an electrical sheath 152. Sockets 154 are disposed at one end in the insulator 150 at positions around the female terminals 148. The terminals 148 are sealed to the insulator 150 by ceramic material 156 and the sheath 152 is sealed to the insulator 150 by ceramic material 158.

A sealing member generally indicated at 160 is provided with bores 162 so that the pins 134 can be extended through the bores to mate with the female terminals 148. The sealing member 160 is also provided with projections 164 and 166 at opposite ends of the member. The projections 166 mate with the socket 154 and the projections 164 mate with the sockets 140.

When the male member 130, the sealing member 160 and the female 132 are assembled, a sealing relationship is produced between the various members. This causes a water-resistant electrical connector to be produced. The electrical connector is noncorrosive because it is made from different materials each of which is noncorrosive. The electrical connector is operative even in salt water without any problems of shorting. Furthermore, the electrical connector is operative under wide ranges of temperature and pressure without any deleterious effect.

FIG. 9 shows an arrangement for providing a grease plug. The grease plug includes a first member generally indicated at 170 and a second member generally indicated at 172. The member 170 includes a block 174 constituting an electrical insulator. Bores 176 are provided in the block 174 to receive male pins 178. The member 170 also includes a threaded bore 180 for receiving an externally threaded drive screw 182.

The member 172 includes a body 184 made from an electrically insulated material and provided with sockets 186. Female conductors 188 are disposed in the sockets 186 in loosely disposed relationship to the sockets. Ducts 190 extend to the sockets 186 from a grease plug 192 containing a flowable grease. The member 184 is also provided with a threaded bore 194.

The pins 178 are sealed to the block 174 by a suitable ceramic material 198. Similarly, the female conductors 188 are sealed to the body 184 by ceramic material 198. As previously described, the members 174 and 184, the pins 178 and the female conductors 188 and the ceramic material 196 and 198 may be provided with substantially the same coefficient of thermal expansion.

When the drive screw is rotated to move the members 174 and 184 into abutting relationship, the grease from the plug 192 flows through the ducts 190 and the sockets 186 to the planar surface common to the members 174 and 184. Any excess grease flow from the surface between the members is indicated at 200. The grease flowing through the sockets 186 and along the surface between the members 174 and 184 displaces salt water and provides electrical insulation even when the electrical connector is disposed in water. Furthermore, the watertight relationship is maintained over extended periods of time since the materials in the electrical connector are noncorrosive. The watertight relationship is also maintained in the electrical connector even under a wide range of temperatures and pressures.

Figure 10:
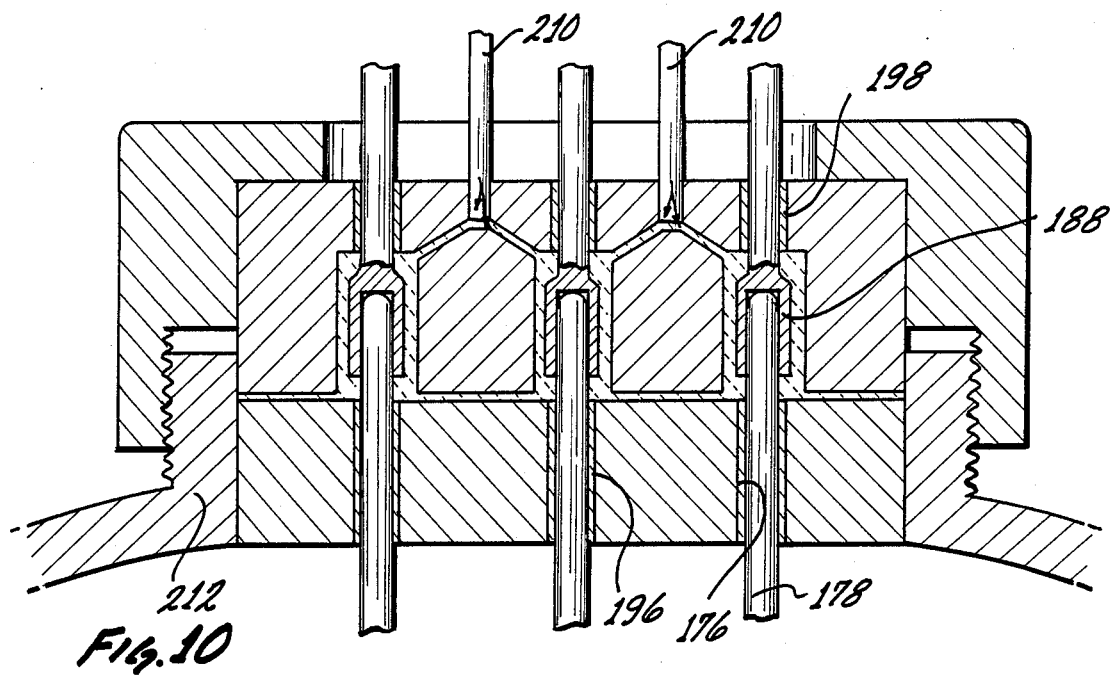
FIG. 10 is a sectional view of another embodiment of the invention.

FIG. 10 illustrates an arrangement similar to that shown in FIG. 9. However, in the embodiment of FIG. 10, grease is introduced into the electrical connector from an external source through grease fittings 210. Furthermore, the two members are pressed together by a threaded arrangement 212 peripherally disposed relative to the members.

FIG. 11 illustrates an embodiment similar in a number of respects to several of the embodiments shown above and discussed previously. The embodiment of FIG. 11 includes a casing 240 made from a suitable material such as the alloy of magnesium oxide, silica and alumina. The casing 240 is provided internally with a cavity 242. Electronic equipment is disposed in the cavity 242 and is provided with electrical leads 244. The leads 244 are extended through bores 246 in the casing 240. The casing 240 is preferably provided with a soxket 248 at the end through which the leads 244 are extended.

A cover 250 is also made from the insulating material such as the alloy of magnesium oxide, silica and alumina. The cover 250 is provided with a cap portion 252 which is seated in the socket 248. The cover 250 is also provided with bores 254 through which terminals 256 are extended. The terminals 256 are connected to the leads 244 and may be made from a suitable material such as platinum, titanium or a titanium alloy.

Ceramic material 258 is disposed in a pocket extending around the cover 250 at a position between the cover and the casing 240. The ceramic material 258 is bonded to the cover 250 and to the casing 240 to maintain the cover and the casing in hermetically sealed relationship. Ceramic material 260 is also disposed in the bores 254 to bond the terminals 256 to the cover 250 in a hermetically sealed relationship.

Figure 12:
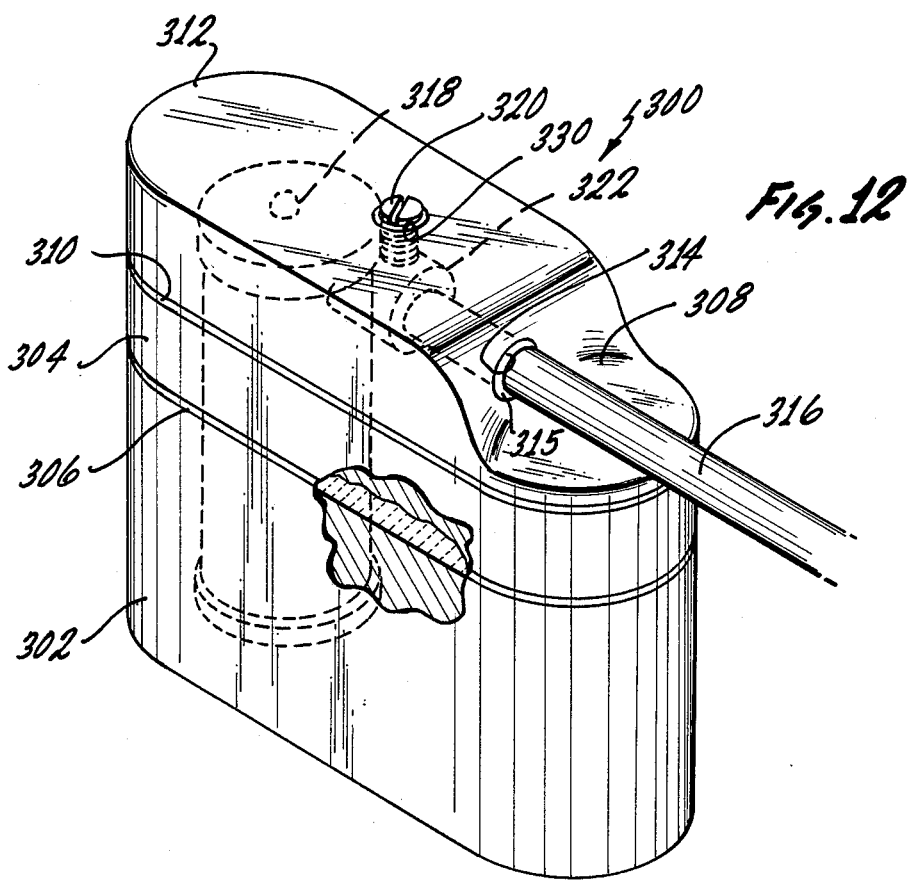
FIG. 12 is a perspective view, partially broken away, of an additional embodiment of the invention.

FIG. 12 illustrates a embodiment of a heart pacemaker generally indicated at 300. The pacemaker includes a metal housing 302 made from a suitable material such as titanium or a titanium alloy. A housing 304 made from substantially the same insulating material as the insulating material 12 of FIG. 1 is disposed on the housing 302 and is sealed to the housing as at 306 by ceramic material. A lid 308 made from a suitable electrical conductor such as titanium or a titanium alloy is in turn sealed as by a ceramic material 310 to the insulating housing 304.

A cover 312 made from the insulating material is disposed on the lid 308 and is sealed to the lid by ceramic material. The cover 312 is provided with an opening 314 to receive an input lead 316 made from a suitable electrical conductor such as platinum. The lead 316 communicates electrically with a terminal 318 which extends through the lid 308 from the interior of the pacemaker 300. The lead 316 is connected to the heart to provide stimulation to the heart at a particular frequency. The lead 316 is sealed in the opening 314 by ceramic material 315 which is bonded to the lead 316 and to the cover 312.

Proper electrical continuity is assured between the lead 316 and the terminal 318 by a set screw 320 which extends through a threaded socket 322 in the top of the cover 312. The set screw 320 is rotated in a direction to press the lead 316 against the terminal 318. This assures proper electrical contact between the lead 316 and the terminal 318. The set screw 320 is then sealed within the cover 312 by ceramic material 330.

As will be seen, the heart pacemaker is sealed within the casing defined by the housings 302 and 304, the lid 308 and the cover 312. Furthermore, the casing is formed by materials which are not considered by the body of the patient to be foreign. This provides for the retention of the heart pacemaker within the body of the patient without any adverse effects to the body of the patient. It also provides for the disposition of the heart pacemaker within the body under variable conditions of temperature and pressure and without any corrosion of the casing or without any chemical reactions of the casing with the chemicals of the patient's body. It further provides for the retention of the heart pacemaker within the body in a hermetically sealed relationship.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination, an electrical conductor having a particular coefficient of thermal expansion and having non-corrosive properties,
an electrical insulator disposed in spaced relationship to the electrical conductor and having a coefficient of thermal expansion closely approximating the particular coefficient of thermal expansion, and
a ceramic material having electrically insulating properties and disposed between the electrical conductor and the electrical insulator in sealed relationship with the electrical conductor and the electrical insulator and having a melting temperature above 1200° F. and having a coefficient of thermal expansion closely approximating the particular coefficient of thermal expansion and hermetically sealed to the electrical conductor and the electrical insulator even when subjected to temperatures as high as 1200° F. for extended periods of time such as approximately one hundred (100) hours,
the electrical insulator having a different composition than the ceramic material.

2. The combination set forth in claim 1 wherein the electrical conductor is disposed in enveloping relationship to the electrical insulator and the ceramic material is partially amorphous and partially crystalline and is disposed between the electrical conductor and the electrical insulator in the enveloping relationship.

3. The combination set forth in claim 1 wherein the ceramic material has a high electrical resistivity and is highly resistant to strong acids and bases.

4. The combination set forth in claim 1 wherein the electrically insulating ceramic material bonds the electrical conductor and the electrical insulator to form a hermetic seal between the electrical conductor and the electrical insulator.

5. The combination set forth in claim 4 wherein the ceramic material has properties of flowing between the electrical insulator and the electrical conductor and bonding the electrical insulator and the electrical conductor when subjected to heat.

6. The combination set forth in claim 1 wherein a second electrical conductor formed from a material different from the first electrical conductor is disposed in closely spaced relationship to the electrical insulator and
additional amounts of the electrically insulating ceramic material are disposed between the electrical insulator and the second electrical conductor and are bonded to the electrical insulator and the second electrical conductor to form a hermetic seal with the electrical insulator and the second electrical conductor.

7. The combination set forth in claim 6 wherein the first electrical conductor is platinum,
the second electrical conductor is selected from the group consisting of titanium and a titanium alloy and
the electrical insulator is Fosterite.

8. The combination set forth in claim 7 wherein the ceramic material is made from an alloy including materials containing antimony, zinc, zirconium and oxygen.

9.
a first electrical conductor having a particular coefficient of thermal expansion,
a second electrical conductor having a coefficient of thermal expansion closely approximating the particular coefficient of thermal expansion and made from a different material than the first electrical conductor,
an electrical insulator having a coefficient of thermal expansion closely approximating the particular coefficient of thermal expansion and formed at least partially from metallic oxides and disposed in spaced relationship to the electrical conductor, and
a ceramic material providing an electrical insulation and disposed between the first electrical conductor and the electrical insulator and between the second electrical conductor and the electrical insulator and hermetically sealed to the first and second electrical conductors and the electrical insulator and having a coefficient of thermal expansion closely approximating the particular coefficient of thermal expansion,
the ceramic material being partially amorphous and partially crystalline.

10. The combination set forth in claim 9 wherein the composition of the electrical conductors, the electrical insulator and the ceramic material are compatible with the human body even when the electrical conductors, the electrical insulator and the ceramic material are implanted within the human body.

11. The combination set forth in claim 9 wherein the ceramic material includes the oxide of lead and the electrical conductor, the electrical insulator and the ceramic material have properties preventing any leaching of lead from the ceramic material.

12.
a first electrical conductor having a particular coefficient of thermal expansion,
a second electrical conductor having a coefficient of thermal expansion closely approximating the particular coefficient of thermal expansion and made from a different material than the first electrical conductor,
an electrical insulator having a coefficient of thermal expansion closely approximating the particular coefficient of thermal expansion and formed at least partially from metallic oxides and disposed in spaced relationship to the electrical conductor, and
a ceramic material providing an electrical insulation and disposed between the first electrical conductor and the electrical insulator and between the second electrical conductor and the electrical insulator and hermetically sealed to the first and second electrical conductors and the electrical insulator and having a coefficient of thermal expansion closely approximating the particular coefficient of the thermal expansion,
the ceramic material providing a hermetic seal with the electrical conductors and the electrical insulator upon an application to the ceramic material, without any prior treatment of the electrical conductors or the electrical insulator, of heat providing a temperature above 1200° F.

13. In combination,
an electrical conductor having a particular coefficient of thermal expansion,
an electrical insulator disposed in spaced relationship to the electrical conductor and having a coefficient of thermal expansion closely approximating the particular coefficient of thermal expansion, and
a ceramic material providing an electrical insulation and disposed between the electrical conductor and the electrical insulator and hermetically sealed to the electrical conductor and the electrical insulator and having a coefficient of thermal expansion closely approximating the particular coefficient of thermal expansion and having a partially amorphous and a partially crystalline composition and hermetically sealed to the electrical conductor and the electrical insulator through an extended range of temperatures as high as 1200° F.,
the ceramic material having a different composition than the insulating material.

14. The combination set forth in claim 13 wherein the ceramic material has a melting temperature above 1200° F. and produces the hermetic seal with the electrical conductor and the electrical insulator when heated to a temperature above its melting temperature.

15. The combination set forth in claim 13 wherein the compositions of the electrical conductor, the electrical insulator and the ceramic material are compatible with the human body even when the electrical conductor, the electrical insulator and the thin film are implanted in the human body.

16. The combination set forth in claim 13 wherein the ceramic material is highly resistant to strong acids and bases and has a high electrical resistivity.

17. The combination set forth in claim 13 wherein the ceramic material includes the oxide of lead and the electrical conductor, the electrical insulator and the ceramic material have properties preventing any leaching of lead from the ceramic material.

18. In combination,
an electrical conductor having a particular coefficient of thermal expansion,
the electrical material being made from a material selected from the group consisting of platinum, titanium and titanium alloys,
an electrical insulator made from Fosterite and having a coefficient of thermal expansion closely approximating the particular coefficient of thermal expansion and disposed in closely spaced relationship to the electrical conductor, and
a ceramic material providing an electrical insulation and disposed between the electrical conductor and the electrical insulator and having a coefficient of thermal expansion closely approximating the particular coefficient of thermal expansion and providing a hermetic seal with the electrical conductor and the electrical insulator through an extended range of temperatures, without any prior treatment of the electrical conductor or the electrical insulator, upon an application of heat above a temperature of 1200° F. to the ceramic material, the electrical conductor and the electrical insulator,
the ceramic material having a different composition than the electrical insulator.

19. The combination set forth in claim 12 wherein the ceramic material provides a hermetic seal with the electrical conductor and the electrical insulator through an extended range of temperatures upon an application of heat to the ceramic material to a temperature between approximately 1500° F. and 1750° F.

20. The combination set forth in claim 19 wherein the ceramic material is formed from first and second fluxes each containing oxides of lead and boron and is further formed from a polycrystalline stuffing containing oxygen combined with zinc, zirconium and antimony.

21. The combination set forth in claim 20 wherein one of the fluxes also contains the oxide of silicon.

22. The combination set forth in claim 21 wherein the first electrical conductor constitutes a terminal pin made from platinum and
the electrical insulator envelopes the terminal pine and
a second electrical conductor envelopes the electrical insulator in spaced relationship to the electrical insulator and the second electrical conductor is made from a material selected from the group consisting of titanium and a titanium alloy and
the ceramic material is disposed between the electrical insulator and the second electrical conductor and is hermetically sealed to the electrical insulator and the second electrical conductor.

23. The combination set forth in claim 20 wherein the first and second fluxes provide a eutectic relationship.

24. The combination set forth in claim 12 wherein the ceramic material is formed from first and second fluxes and a polycrystalline stuffing.

25. In combination, an electrical conductor having a particular coefficient of thermal expansion, an electrical insulator disposed in spaced relationship to the electrical conductor and having a coefficient of thermal expansion closely approximating the particular coefficient of thermal expansion, and a ceramic material disposed between the electrical conductor and the electrical insulator and having a coefficient of thermal expansion closely approximating the particular coefficient of thermal expansion and hermetically sealed to the electrical conductor and the electrical insulator through an extended range of temperatures, the compositions of the electrical conductor, the electrical insulator and the ceramic material being compatible with the human body even when the electrical conductor, the electrical insulator and the ceramic material are implanted in the human body, the ceramic material having a different composition than the electrical insulator.

26. The combination set forth in claim 25 wherein
the ceramic material includes the oxide of lead and
the electrical conductor, the electrical insulator and the ceramic material have properties preventing any leaching of lead from the ceramic material.

27. The combination set forth in claim 26 wherein
the ceramic material is partially amorphous and partially crystalline.

28. The combination set forth in claim 27 wherein
the ceramic material includes the oxides of lead and boron and further includes oxygen combined with zinc, zirconium and antimony.

29. The combination set forth in claim 28 wherein
the insulating material is Fosterite and the electrical conductor is made from a material selected from the group consisting of platinum, titanium and a titanium alloy.

30. In combination,
an electrical conductor having a particular coefficient of thermal expansion, an electrical insulator disposed in spaced relationship to the electrical conductor and having a coefficient of thermal expansion closely approximating the particular coefficient of thermal expansion, and a ceramic material providing an electrical insulation and disposed between the electrical conductor and the electrical insulator and hermetically sealed to the electrical conductor and the electrical insulator, the ceramic material including the oxide of lead, the ceramic material, the electrical conductor and the electrical insulator having properties preventing any leaching of lead from the ceramic material, the ceramic material having a different composition than the electrical insulator.

31. The combination set forth in claim 30 wherein
the ceramic material is partially amorphous and partially crystalline.

32. The combination set forth in claim 31 wherein
the ceramic material is formed from a first flux containing the oxides of lead and boron, a second flux containing the oxides of lead, boron and silicon and a polycrystalline stuffing containing oxygen combined with zinc and zirconium.

* * * * *